(12) United States Patent
Driessens et al.

(10) Patent No.: US 6,206,957 B1
(45) Date of Patent: Mar. 27, 2001

(54) TRICALCIUM PHOSPHATE-CONTAINING BIOCEMENT PASTES COMPRISING COHESION PROMOTERS

(75) Inventors: Ferdinand C. M. Driessens; Robert Wenz, both of Darmstadt (DE)

(73) Assignee: Merck Patent Gesellschaft mit beschrankter Haftung, Darmstadt (DE)

(*) Notice: Subject to any disclaimer, the term of this patent is extended or adjusted under 35 U.S.C. 154(b) by 0 days.

(21) Appl. No.: 09/292,952

(22) Filed: Apr. 16, 1999

(30) Foreign Application Priority Data

Apr. 16, 1998 (DE) .............................. 198 16 858

(51) Int. Cl.$^7$ ..................................... A61L 25/00
(52) U.S. Cl. ................. 106/35; 433/228.1; 427/2.26; 427/2.27; 424/687; 424/602; 424/603
(58) Field of Search ............................ 106/35; 424/687, 424/602, 603; 427/2.27, 2.26; 433/228.1

(56) References Cited

U.S. PATENT DOCUMENTS

| | | | |
|---|---|---|---|
| 4,518,430 | 5/1985 | Brown et al. | 106/35 |
| 4,612,053 | 9/1986 | Brown et al. | 433/328.1 |
| 4,880,610 | 11/1989 | Constantz | 423/305 |
| 5,053,212 | 10/1991 | Constantz et al. | 423/305 |
| 5,152,836 | * 10/1992 | Hirano et al. | 106/690 |
| 5,281,404 | * 1/1994 | Sumita et al. | 501/1 |
| 5,605,713 | 2/1997 | Boltong | 427/2.1 |

FOREIGN PATENT DOCUMENTS

| | | |
|---|---|---|
| 0416761A1 | 3/1991 | (EP) . |
| 0543765A1 | 5/1993 | (EP) . |
| 0664133A1 | 7/1995 | (EP) . |
| 2-275812 | * 11/1990 | (JP) . |
| 4-12044 | * 1/1992 | (JP) . |
| 96/36562 | 11/1996 | (WO) . |

OTHER PUBLICATIONS

Jansen et al., *J.Mat.Science Mat. in Medicine 6*, "Evaluation of tricalciumphosphate/hydroxyapatite cement for tooth replacement: an experimental animal study", 1995.

Ishikawa, *J.Mat. Science Mat. in Medicine 6*, "Properties and mechanisms of fast–setting calcium phosphate cements", pp. 528–533, (1995).

Bermúdez et al., *J. Mat. Science Mat. in Medicine 4*, "Compressive strength and diametral tensile strength of some calcium–orthophosphate cements: a pilot study", pp. 389–383, (1993).

Kurashima et al., *Biomaterials 18*, "In vivo study of calcium phosphate cements: implantation of an α–tricalcium phosphate/dicalcium phosphate dibasic/tetracaclium phosphate monoxide cement paste", pp. 539–543, (1997).

Driessens et al., *J. Mat. Science Mat. in Medicine 4*, "Formulation and setting times of some calcium orthophosphate cements: a pilot study", pp. 503–508, (1993).

Fernández et al. *J. Mat. Science Letters 15*, "Development of a method to measure the period of swelling of calcium phosphate cements", pp. 1004–1005, (1996).

A. Cherng, S. Takagi L.C. Chow, "Effects of hydroxypropyl methylcellulose and other gelling agents on the handling properties of calcium phosphate cement", *Cellulose Handling Properties of CPC*, pp. 273–277, (1995).

* cited by examiner

Primary Examiner—C. Melissa Koslow
(74) Attorney, Agent, or Firm—Millen, White, Zelano & Branigan

(57) ABSTRACT

The invention relates to biocement pastes based on tricalcium phosphate and materials which are suitable for preventing or reducing the tendencies of the settable pastes to disintegrate and for improving their cohesion properties, with the result that improved processing of said pastes in the preparation of synthetic bone cements is ensured.

17 Claims, No Drawings

TRICALCIUM PHOSPHATE-CONTAINING BIOCEMENT PASTES COMPRISING COHESION PROMOTERS

SUMMARY OF THE INVENTION

The invention relates to biocement pastes based on tricalcium phosphate and materials which are suitable for preventing or reducing the tendencies of the settable pastes to disintegrate and for improving their cohesion properties, with the result that improved processing of pastes in the preparation of synthetic bone cements is ensured. The invention relates further to biocement pastes comprising cohesion promoters. The cohesion promoters are preferably selected from the following compounds or classes of compounds: hydroxyethyl starch, cyclodextrins, alginates, dextran sulphates, polyvinylpyrrolidone and hyaluronic acid.

The advantage of the pastes according to the invention is that they do not become inhomogeneous or dissolve when they come into contact with aqueous solutions, such as saline solutions, and body fluids, such as, for example, blood. Furthermore, such pastes do not disintegrate or do so only to a greatly reduced extent when they are injected by means of syringes, as a rule at superatmospheric pressure, into the defective bone space.

Naturally occurring bone material consists of calcium phosphate having the hydroxyapatite structure. However, the composition of bone minerals does not correspond to the ideal stoichiometric composition of crystalline hydroxyapatite ($Ca_{10}(PO_4)_6(OH)_2$) but as a rule has a nonstoichiometric composition which is due to the incorporation of other anions, such as carbonate or hydrogen phosphate, instead of orthophosphate, but also of other cations, such as sodium, potassium or magnesium, instead of calcium.

For some years it has been possible to prepare synthetic bone material based on hydroxyapatite-like calcium phosphate compounds which, owing to its qualitative and structural similarities, very closely resembles natural bone. The known disadvantages which may occur as a result of acquiring natural autogenous or heterogeneous bone can thus be avoided. Synthetic calcium phosphate cements can be used in diverse and different ways, for example for bone fractures, fixation of metal prostheses and bone screws, in the dental sector and in plastic surgery.

The properties of these synthetic hydroxyapatites or calcium phosphate cements (CPC), in particular their physiological acceptance, the required bioabsorbability and the ability to be replaced by newly generated natural bone tissue or stimulation of the growth thereof, depend on the more or less strongly pronounced crystallinity, on the particle size and on the porosity which can be achieved in the preparation. Furthermore, these materials have the advantage that they withstand mechanical loads virtually as well as the natural bone, which suggests their use for relatively large bone defects or bone fractures.

The main components of these materials are, for example, tricalcium phosphate (alpha- and beta-TCP), dicalcium phosphate (DCP) and tetracalcium phosphate (TTCP), which, in the presence of water, react to give hydroxyapatite, the end product of the cement formation reaction. Since hydroxyapatite formed in this manner has formed in an aqueous environment, it resembles the biological apatites to a far greater extent than the hydroxyapatite which is produced at high temperatures. Such cements are therefore osteotransductive and hence very suitable for repairing and reconstructing bones. They are rapidly integrated in bone structures and then converted into new bone tissue by the cellular activity of the osteoblasts.

Such cements are disclosed, for example, in U.S. Pat. No. 4,518,430, U.S. Pat. No. 4,612,053, U.S. Pat. No. 4,880,610, U.S. Pat. No. 5,053,212, U.S. Pat. No. 5,152,836, U.S. Pat. No. 5,605,713, EP 0416 761, EP 0 543 765, EP 0664 133 or WO 96/36562. WO 96/36562 discloses a hydroxyapatite bone cement (α-BSM) which, owing to its virtually amorphous structure, has excellent bioabsorbability and, in spite of its porosity, good mechanical stability. This and many of the materials described in the above-mentioned publications can be prepared in the form of settable pastes which can be easily introduced into the defective bone by means of a syringe.

However, it has now been found that such pastes often partially or completely disintegrate or exhibit inhomogeneous behavior as soon as they come into contact with body fluids or other aqueous solutions (Jansen et al., 1995, J. Mater. Sci. Mat. Med. 6, 653; Ishikawa et al., 1995, J. Mater. Sci. Mat Med. 6, 528; Kurashina et al., 1997, Biomaterials 18, 539). Furthermore, such pastes readily separate during extrusion from syringes, the more liquid part being forced out of the syringe while the more solid part remains in the syringe and cannot be removed from it even by means of higher pressures. As a result of the separation, a material which is no longer suitable for the intended purpose may thus be obtained.

Cherng et al. (J. Biomed. Mat. Res. 35, 1997, page 273) and Chow et al. (Innov. Techn. Biol. Med. 18, 1997, page 11) report the use of hydroxypropylmethylcellulose and carboxymethylcellulose and chitosan derivatives in calcium phosphate cements based on tetracalcium phosphate (TTCP). The additives lead to improved processing properties with regard to the cohesion of the cement pastes used but frequently result in poorer setting kinetics and reduced mechanical strength of the set cements.

It was therefore an object of the invention to provide cement pastes which lead to settable, biocompatible synthetic bone cements and which not only have substantially improved cohesion properties but also possess sufficient or advantageous injectability, mechanical hardness and setting times.

Upon further study of the specification and appended claims, further objects and advantages of this invention will become apparent to those skilled in the art.

These objects are achieved by the pastes of the present invention.

The invention therefore relates to a processible, settable paste, suitable for the preparation of biocompatible bone cements, which can be obtained by mixing a cement powder which contains tricalcium phosphate (TCP) and at least one further calcium phosphate-containing compound with an aqueous solution of a cohesion promoter and a setting accelerator. As used herein, the term "processible" means a paste which can be processed or treated, e.g., injected with a syringe.

According to the invention, the cohesion promoters are used in a concentration of about 0.1 to 10% (wt/wt), preferably about 1 to 6% (wt/wt), based on the aqueous solution before the paste is formed. The corresponding compounds are dissolved in water. If required, small amounts of organic solvents may be present if the cohesion promoter is poorly soluble in pure water.

Suitable cohesion promoters are in principle all compounds known for this object, in particular oligomeric and/or polymeric compounds. Preferably, compounds for use as cohesion promoters are selected from the celluloses, for example hydroxyethylcellulose, hydroxymethylcellulose, hydroxypropylmethylcellulose or carboxymethylcellulose, preferably hydroxyethyl starch and soluble starch, cyclodextrins, such as α-, β- or γ-cyclodextrin, alginates, such as sodium alginate, dextransulphates, such as sodium dextransulphate, polyvinylpyrrolidone and hyaluronic acid. According to the invention, several cohesion promoters can also be used.

The pastes according to the invention furthermore contain setting accelerators, for example $Na_2HPO_4$, $NaH_2PO_4$, $KH_2PO_4$, $K_2HPO_4$, or mixtures thereof, in concentrations of about 0.5 to 5% (wt/wt). The concentration depends on the choice of the cohesion promoter but especially on the composition of the calcium phosphate cement in conjunction with the desired medical application.

Furthermore, the ratio of liquid to cement powder which are mixed with one another affects the cohesion and injectability properties of the pastes according to the invention. Preferably, the ratio of aqueous solution to cement powder is about 0.30 to 0.45 ml/g, in particular about 0.35 to 0.40 ml/g.

Surprisingly, it has been found that one can avoid or reduce some of the adverse properties of cement mixtures which have been described in the prior art, such as lowered strength or prolonged setting times, by including tricalcium phosphate (TCP), in particular α-TCP, in the cement mixture. This advantage occurs even if cohesion-promoting compounds similar to those of the prior art are used. Preferably at least one further calcium phosphate-containing compound, preferably precipitated hydroxyapatite (PHA), is present. One type of PHA is, for example, Merck Tricalcium phosphate, catalogue No. 2143. Cement mixtures which therefore contain α-TCP and PHA are preferred. Furthermore, mixtures which contain α-TCP, PHA and dicalcium phosphate DCP) are preferred, as well as mixtures which each additionally contain calcium carbonate. By adding said setting accelerators in different concentrations, more rapidly or more slowly settable cements having sufficiently high mechanical strength can be obtained in an individual manner after setting is complete in the case of pastes according to the invention, depending on the desired clinical application.

The invention therefore also relates to a corresponding paste, in which the calcium phosphate cement powder has the following components:

(i) α-tricalcium phosphate (α-TCP), precipitated hydroxyapatite (PHA) or (ii) α-TCP, PHA, dicalcium phosphate (DCP) or (iii) α-TCP, PHA, DCP, $CaCO_3$ or (iv) α-TCP, PHA, $CaCO_3$.

In a particular embodiment, the invention relates to a corresponding paste, in which the calcium phosphate cement powder has the following components:

(i) α-TCP (90 to 99%), PHA (1 to 10%) or (ii) α-TCP (55 to 80%), PHA (1 to 15%), DCP (10 to 40%) or (iii) α-TCP (50 to 80%), PHA (1 to 15%), DCP (10 to 40%), $CaCO_3$ (1 to 12%) or (iv) α-TCP PHA (80 to 98%), PHA (1 to 15%), $CaCO_3$ (1 to 12%).

In a further embodiment, the invention relates to a corresponding paste, in which the calcium phosphate cement powder has the following components:

(i) α-TCP (98%), PHA (2%) or (ii) α-TCP (64%), PHA (9%), DCP (27%) or (iii) α-TCP (58%), PHA (8.5%), DCP (25%), $CaCO_3$ (8.5%) or (iv) α-TCP (90%), PHA (5%), $CaCO_3$ (5%).

The pastes according to the invention are preferably prepared by dissolving the cohesion promoters and setting accelerators in the desired stated concentrations in water or water-containing mixtures. This cement liquid is then mixed or stirred with the cement powder mixture to give a paste.

Finally, the invention therefore further relates to a process for the preparation of a calcium phosphate-containing cement paste having improved cohesion properties, which is characterized in that a cement powder which contains tricalcium phosphate (TCP) and at least one further calcium phosphate-containing compound is mixed with an aqueous solution of a cohesion promoter in a concentration of about 0.1 to 5% (wt/wt), based on the liquid phase before the paste is formed, it being possible, depending on the desired medical application, to adjust the setting kinetics individually by using a setting accelerator in a concentration of about 0.2 to 5% (wt/wt), based on the liquid phase before the paste is formed.

According to the invention, the term "cohesion time" (CT) is understood as meaning the time span between mixing of the powder and of the liquid and the moment when the paste no longer disintegrates when it is immersed for 24 h in Ringer's solution (Fernandez et al., 1996, J. Mater. Sci. Letters 15, 1004).

According to the invention, the term "injectability" is understood as meaning the percentage by weight of the amount of calcium phosphate paste between 2 and 4 g which is extruded from a 20 ml syringe with a force of not more than 100 N within 2 min from the beginning of mixing.

In the case of the setting time, a distinction is made between two terms, i.e. the time when the setting has begun ("Initial Setting Time", IT) and the time when the setting is complete ("Final Setting Time", FT). According to the invention, the IT is measured with the aid of the thick and light Gilmore needle and the FT with the thin and heavy Gilmore needle (Driessens et al., 1993, J. Mater. Sci. Mat. Med. 4, 503).

According to the invention, the mechanical strength or compressive strength is measured after immersion of the set paste for three days in Ringer's solution at 37° C. (Bermudez et al., 1993, J. Mater. Sci. Mat. Med. 4, 389).

According to the invention, the preferably oligomeric/polymeric cohesion promoters and the setting accelerator or accelerators are dissolved or suspended in the cement liquid and this solution is mixed with the powder mixture based on TCP to give a processible paste. A processible paste can be obtained only if a specific ratio of liquid to powder is maintained. According to the invention, this ratio (ml/g) is about 0.25 to 0.50, preferably about 0.3 to 0.45, particularly preferably about 0.35 to 0.40. After mixing to give a processible paste, the latter can be either introduced directly into the implantation site or filled into a syringe from which it is injected into the implantation site before the "Initial Setting Time" is reached, i.e. before the paste begins to set.

In the foregoing and in the following examples, all temperatures are set forth uncorrected in degrees Celsius; and, unless otherwise indicated, all parts and percentages are by weight.

The entire disclosure of all applications, patents and publications, cited above and below, and or corresponding Germany Application No. 198 16858.6, filed Apr. 16, 1998, is hereby incorporated by reference.

EXAMPLES

Below, the invention is described in more detail with reference to Examples without being restricted thereby. The composition of the calcium phosphate cements (CPC) used is shown in Table 1.

TABLE 1

| CPC | Percentage amount (% by weight) | | | |
|---|---|---|---|---|
| | α-TCP | PHA | DCP | CaCO$_3$ |
| Biocement H | 98 | 2 | | |
| Biocement F | 64 | 9 | 27 | |
| Biocement B | 90 | 5 | | 5 |
| Biocement D | 58 | 8.5 | 25 | 8.5 |

In all examples in which cohesion promoters are added, Na$_2$HPO$_4$ (1%) is used as a setting accelerator. In these examples, the effect of the various cohesion promoters on the stated biocements is investigated. The measured parameters in each case are:

L/P=Liquid/powder ratio in ml/g;

CT=Cohesion time in min (as defined above);

IT="Initial Setting Time" in min (as defined above);

FT="Final Setting Time" in min (as defined above);

CS="Compressive Strength" in MPa (as defined above);

IJ=Injectability in % (as defined above).

The mechanical strength of the set cements is substantially independent of the concentration of the setting accelerator (at least up to 4%). An exception in this respect is the biocement H. Thus, the CS value decreases from 55 MPa with 0% of Na$_2$HPO$_4$ continuously to 27 MPa with 4% of Na$_2$HPO$_4$.

Example 1

Effect of Hydroxyethyl Starch (HES) (1.5% by Weight, Based on the Total Amount of Cement Powder) on Various Biocements

| Biocement | L/P (ml/g) | HES | CT (min) | IT (min) | FT (min) | CS (MPa) | IJ (%) |
|---|---|---|---|---|---|---|---|
| H | 0.35 | − | 8 | 12 | 30 | 48 | 53 |
| | | + | 1.3 | 14.5 | >45 | 37 | 60 |
| | 0.40 | − | 11 | 20 | 58 | 35 | 75 |
| | | + | 1.3 | 22 | >45 | 34 | 78 |
| F | 0.35 | − | 8 | 10 | 20 | 33 | 89 |
| | | + | 4 | 11 | 26 | 27 | 89 |
| | 0.40 | − | 10 | 12.5 | 29 | 22 | 93 |
| | | + | 1.5 | 16 | >45 | 23 | 94 |
| B | 0.35 | − | 9 | 16 | 34 | 43 | 76 |
| | | + | 1.75 | 14.5 | 32 | 56 | 72 |
| | 0.40 | − | 13.5 | 21 | 42 | 43 | 90 |
| | | + | 1.5 | 19 | >45 | 43 | 90 |
| D | 0.35 | − | 10 | 16 | 24 | 45 | 91 |
| | | + | 1.25 | 12 | 27.5 | 42 | 91 |
| | 0.40 | − | 13 | 18 | 34 | 38 | 94 |
| | | + | 1.5 | 18.5 | 50 | 33 | 91 |

Example 2

Effect of Sodium Dextransulphate (SDS) (4% by Weight, Based on the Total Amount of Cement Powder) on Various Biocements

| Biocement | L/P (ml/g) | SDS | CT (min) | IT (min) | FT (min) | CS (MPa) | IJ (%) |
|---|---|---|---|---|---|---|---|
| H | 0.35 | − | 8 | 12 | 30 | 39 | 53 |
| | | + | 1.25 | 8.5 | 25 | 30 | 36 |
| | 0.40 | − | 11 | 20 | 58 | 30 | 75 |
| | | + | 1.25 | 13 | 35 | 27 | 88 |
| F | 0.35 | − | 8 | 10 | 20 | 29 | 89 |
| | | + | 3 | 8 | 31 | 37 | 91 |
| | 0.40 | − | 10 | 12.5 | 29 | 22 | 93 |
| | | + | 2 | 10 | 38 | 28 | 90 |
| B | 0.35 | − | 9 | 16 | 34 | 24 | 76 |
| | | + | 3 | 9 | 20.5 | 35 | 85 |
| | 0.40 | − | 13.5 | 21 | 42 | 21 | 90 |
| | | + | 1.75 | 12 | 43 | 28 | 95 |
| D | 0.35 | − | 10 | 16 | 24 | 40 | 91 |
| | | + | 4 | 8.5 | 20 | 39 | 94 |
| | 0.40 | − | 13 | 18 | 34 | 31 | 94 |
| | | + | 1.75 | 9.5 | 28 | 30 | 91 |

Example 3

Effect of β-cyclodextrin (β-CD) (1% by Weight, Based on the Total Amount of Cement Powder) on Various Biocements

| Biocement | L/P (ml/g) | β-CD | CT (min) | IT (min) | FT (min) | CS (MPa) | IJ (%) |
|---|---|---|---|---|---|---|---|
| H | 0.35 | − | 8 | 12 | 30 | 39 | 53 |
| | | + | 1.25 | 10.5 | 26 | 37 | 57 |
| | 0.40 | − | 11 | 20 | 58 | 30 | 75 |
| | | + | 1.25 | 15 | 45 | 32 | 83 |
| F | 0.35 | − | 8 | 10 | 20 | 29 | 89 |
| | | + | 1.5 | 10.5 | 20.5 | 38 | 81 |
| | 0.40 | − | 10 | 12.5 | 29 | 22 | 93 |
| | | + | 2 | 13 | 32 | 27 | 88 |
| B | 0.35 | − | 9 | 16 | 34 | 24 | 76 |
| | | + | 4.5 | 9 | 19 | 33 | 79 |
| | 0.40 | − | 13.5 | 21 | 42 | 21 | 90 |
| | | + | 1.25 | 12.5 | 37 | 26 | 89 |
| D | 0.35 | − | 10 | 16 | 24 | 40 | 91 |
| | | + | 1.25 | 8 | 15 | 39 | 89 |
| | 0.40 | − | 13 | 18 | 34 | 31 | 94 |
| | | + | 2 | 11 | 22.5 | 34 | 93 |

Example 4

Effect of Sodium Alginate (SALG) (1% by Weight, Based on the Total Amount of Cement Powder) on Various Biocements

| Biocement | L/P (ml/g) | SALG | CT (min) | IT (min) | FT (min) | CS (MPa) | IJ (%) |
|---|---|---|---|---|---|---|---|
| H | 0.35 | − | 8 | 12 | 30 | 39 | 53 |
| | | + | 1.5 | 14.5 | 44 | 27 | 36 |
| | 0.40 | − | 11 | 20 | 58 | 30 | 75 |
| | | + | 1.5 | 20.5 | >40 | 26 | 87 |
| F | 0.35 | − | 8 | 10 | 20 | 29 | 89 |
| | | + | 1.5 | 10 | 23 | 17 | 90 |

-continued

| Biocement | L/P (ml/g) | SALG | CT (min) | IT (min) | FT (min) | CS (MPa) | IJ (%) |
|---|---|---|---|---|---|---|---|
| | 0.40 | − | 10 | 12.5 | 29 | 22 | 93 |
| | | + | 1.5 | 15.5 | 38 | 19 | 93 |
| B | 0.35 | − | 9 | 16 | 34 | 24 | 76 |
| | | + | 1.5 | 9.5 | 23 | 24 | 83 |
| | 0.40 | − | 13.5 | 21 | 42 | 21 | 90 |
| | | + | 2 | 10.5 | 31.5 | 24 | 94 |
| D | 0.35 | − | 10 | 16 | 24 | 40 | 91 |
| | | + | 1.5 | 12.5 | 28 | 34 | 83 |
| | 0.40 | − | 13 | 18 | 34 | 31 | 94 |
| | | + | 1.5 | 17 | 42 | 32 | 89 |

Example 5

Effect of Soluble Starch (SST) (2% by Weight, Based on the Total Amount of Cement Powder) on Various Biocements

| Biocement | L/P (ml/g) | SST | CT (min) | IT (min) | FT (min) | CS (MPa) | IJ (%) |
|---|---|---|---|---|---|---|---|
| H | 0.35 | − | 8 | 12 | 30 | 39 | 53 |
| | | + | 5 | 15 | >40 | 35 | 51 |
| | 0.40 | − | 11 | 20 | 58 | 30 | 75 |
| | | + | 2 | 20 | >40 | 26 | 77 |
| F | 0.35 | − | 8 | 10 | 20 | 29 | 89 |
| | | + | 5 | 8.5 | 26 | 38 | 83 |
| | 0.40 | − | 10 | 12.5 | 29 | 22 | 93 |
| | | + | 1.5 | 14 | 37.5 | 30 | 89 |
| B | 0.35 | − | 9 | 16 | 34 | 32 | 76 |
| | | + | 5 | 9.5 | 21 | 44 | 88 |
| | 0.40 | − | 13.5 | 21 | 42 | 43 | 90 |
| | | + | 1.5 | 12 | 32 | 36 | 90 |
| D | 0.35 | − | 10 | 16 | 24 | 40 | 91 |
| | | + | 1 | 11 | 27 | 47 | 88 |
| | 0.40 | − | 13 | 18 | 34 | 31 | 94 |
| | | + | 1 | 16 | 38 | 38 | 91 |

Example 6

Effect of Polyvinylpyrrolidone (PVP) (6% by Weight, Based on the Total Amount of Cement Powder) on Various Biocements

| Biocement | L/P (ml/g) | PVP | CT (min) | IT (min) | FT (min) | CS (MPa) | IJ (%) |
|---|---|---|---|---|---|---|---|
| H | 0.35 | − | 8 | 12 | 30 | 50 | 53 |
| | | + | 1.5 | 12 | >40 | 44 | 49 |
| | 0.40 | − | 11 | 20 | 58 | 39 | 75 |
| | | + | 1.25 | 13 | >40 | 42 | 86 |
| F | 0.35 | − | 8 | 10 | 20 | 29 | 89 |
| | | + | 5 | 8 | 26 | 30 | 86 |
| | 0.40 | − | 10 | 12.5 | 29 | 22 | 93 |
| | | + | 1.25 | 8.5 | 42 | 24 | 92 |
| B | 0.35 | − | 9 | 16 | 34 | 32 | 76 |
| | | + | 4 | 9 | 32 | 32 | 72 |
| | 0.40 | − | 13.5 | 21 | 42 | 43 | 90 |
| | | + | 5 | 10.5 | 43 | 34 | 92 |
| D | 0.35 | − | 10 | 16 | 24 | 47 | 91 |
| | | + | 5 | 9 | 29 | 35 | 89 |
| | 0.40 | − | 13 | 18 | 34 | 33 | 94 |
| | | + | 1.5 | 11 | 40 | 35 | 92 |

Example 7

Effect of Potassium Hyaluronate (HAPS) (0.2% by Weight, Based on the Total Amount of Cement Powder) on Various Biocements

| Biocement | L/P (ml/g) | HAPS | CT (min) | IT (min) | FT (min) | CS (MPa) | IJ (%) |
|---|---|---|---|---|---|---|---|
| H | 0.35 | − | 8 | 12 | 30 | 39 | 53 |
| | | + | 1.75 | 12.5 | >40 | 35 | 56 |
| | 0.40 | − | 11 | 20 | 48 | 30 | 75 |
| | | + | 1.5 | 17 | >40 | 33 | 89 |
| F | 0.35 | − | 8 | 10 | 20 | 29 | 89 |
| | | + | 1.5 | 8.5 | 24 | 37 | 82 |
| | 0.40 | − | 10 | 12.5 | 29 | 22 | 93 |
| | | + | 1.75 | 10 | 33 | 27 | 90 |
| B | 0.35 | − | 9 | 16 | 34 | 24 | 76 |
| | | + | 5 | 9 | 23.5 | 37 | 85 |
| | 0.40 | − | 13.5 | 21 | 42 | 21 | 90 |
| | | + | 1.5 | 11 | 31 | 32 | 92 |
| D | 0.35 | − | 10 | 16 | 24 | 40 | 91 |
| | | + | 4 | 8 | 22 | 39 | 91 |
| | 0.40 | − | 13 | 18 | 34 | 31 | 94 |
| | | + | 3 | 9.5 | 34 | 36 | 94 |

Example 8

Effect of α-cyclodextrin (α-CD) (4% by Weight, Based on the Total Amount of Cement Powder) on Various Biocements

| Biocement | L/P (ml/g) | α-CD | CT (min) | IT (min) | FT (min) | CS (MPa) | IJ (%) |
|---|---|---|---|---|---|---|---|
| H | 0.35 | − | 8 | 12 | 30 | 48 | 53 |
| | | + | 1.75 | 13.5 | >40 | 39 | 50 |
| | 0.40 | − | 11 | 20 | 58 | 35 | 75 |
| | | + | 1.75 | 14.5 | >40 | 37 | 79 |
| F | 0.35 | − | 8 | 10 | 20 | 29 | 89 |
| | | + | 4 | 8 | 28 | 31 | 83 |
| | 0.40 | − | 10 | 12.5 | 29 | 22 | 93 |
| | | + | 2 | 13 | 34.5 | 23 | 90 |
| B | 0.35 | − | 9 | 16 | 34 | 38 | 76 |
| | | + | 2.5 | 8 | 23 | 50 | 82 |
| | 0.40 | − | 13.5 | 21 | 42 | 43 | 90 |
| | | + | 1.5 | 12 | 39 | 38 | 89 |
| D | 0.35 | − | 10 | 16 | 24 | 45 | 91 |
| | | + | 2 | 8 | 24 | 46 | 89 |
| | 0.40 | − | 13 | 18 | 34 | 38 | 94 |
| | | + | 1.5 | 15 | 41.5 | 33 | 91 |

Example 9

Effect of γ-cyclodextrin (γ-CD) (2.5% by Weight, Based on the Total Amount of Cement Powder) on Various Biocements

| Biocement | L/P (ml/g) | γ-CD | CT (min) | IT (min) | FT (min) | CS (MPa) | IJ (%) |
|---|---|---|---|---|---|---|---|
| H | 0.35 | − | 8 | 12 | 30 | 39 | 53 |
| | | + | 1.75 | 11 | >40 | 30 | 53 |
| | 0.40 | − | 11 | 20 | 58 | 30 | 75 |
| | | + | 1.75 | 14 | >40 | 34 | 80 |
| F | 0.35 | − | 8 | 10 | 20 | 29 | 89 |
| | | + | 3 | 8.5 | 24 | 27 | 85 |

-continued

| Biocement | L/P (ml/g) | γ-CD | CT (min) | IT (min) | FT (min) | CS (MPa) | IJ (%) |
|---|---|---|---|---|---|---|---|
| | 0.40 | − | 10 | 12.5 | 29 | 22 | 93 |
| | | + | 1.5 | 10 | 33 | 21 | 92 |
| B | 0.35 | − | 9 | 16 | 34 | 24 | 76 |
| | | + | 3 | 9 | 20.5 | 35 | 85 |
| | 0.40 | − | 13.5 | 21 | 42 | 21 | 90 |
| | | + | 1.75 | 12 | 43 | 28 | 95 |
| D | 0.35 | − | 10 | 16 | 24 | 40 | 91 |
| | | + | 4 | 8.5 | 20 | 39 | 94 |
| | 0.40 | − | 13 | 18 | 34 | 31 | 94 |
| | | + | 1.75 | 9.5 | 28 | 30 | 91 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A biocement paste comprising:
   a) tricalcium phosphate,
   b) at least one further calcium phosphate-containing compound,
   c) a cohesion promoter, and
   d) a setting accelerator,
   wherein components a) and b) form a cement powder, and components c) and d) are in an aqueous solution,
   wherein said cement powder is mixed with said aqueous solution to form said biocement paste,
   and wherein said setting accelerator is $Na_2HPO_4$, $NaH_2PO_4$, $KH_2PO_4$, $K_2HPO_4$, or mixtures thereof, in a concentration of 0.5–5% (wt/wt), based on the liquid phase before the paste is formed.

2. The paste according to claim 1, wherein said cement powder comprises tricalcium phosphate and precipitated hydroxyapatite.

3. The paste according to claim 1, wherein the amount of said cohesion promoter in said aqueous solution is 0.1–10% (wt/wt), based on the liquid phase.

4. The paste according to claim 1, wherein said cohesion promoter is hydroxyethyl starch, soluble starch, cyclodextrin, alginate, dextransulphate, polyvinylpyrrolidone or hyaluronic acid.

5. The paste according to claim 1, wherein the ratio of aqueous solution to cement powder is 0.30:1–0.45:1 ml/g.

6. The paste according to claim 1, wherein said cement powder comprises:
   a) α-TCP and PHA,
   b) α-TCP, PHA, and DCP,
   c) α-TCP, PHA, DCP and $CaCO_3$, or
   d) α-TCP, PHA and $CaCO_3$,
   wherein α-TCP is α-tricalcium phosphate, PHA is precipitated hydroxyapatite and DCP is dicalcium phosphate.

7. The paste according to claim 6, wherein said cement powder comprises:
   a) α-TCP (90 to 99%) and PHA (1 to 10%) or
   b) α-TCP (55 to 80%), PHA (1 to 15%), and DCP (10 to 40%),
   c) α-TCP (50 to 80%), PHA (1 to 15%), DCP (10 to 40%) and $CaCO_3$ (1 to 12%) or
   d) α-TCP PHA (80 to 98%), PHA (1 to 15%) and $CaCO_3$ (1 to 12%).

8. A biocement paste according to claim 6, wherein said cement powder comprises
   a) α-TCP (98%) and PHA (2%),
   b) α-TCP (64%), PHA (9%), and DCP (27%),
   c) α-TCP (58%), PHA (8.5%), DCP (25%) and $CaCO_3$ (8.5%) or
   d) α-TCP (90%), PHA (5%) and $CaCO_3$ (5%).

9. The biocement paste according to claim 6, wherein said cohesion promoter is hydroxyethyl starch, soluble starch, cyclodextrin, alginate, dextransulpohate, polyvinylpyrrolidone, or hyaluronic acid.

10. The biocement paste according to claim 8, wherein said cohesion powder in said aqueous solution is in a concentration of 0.1 to 10% (wt/wt), and
   wherein the ratio of aqueous solution to cement powder is 0.30:1–0.45:1 ml/g.

11. A process for the preparation of a calcium phosphate-containing cement paste having improved cohesion properties, comprising mixing a cement powder which contains tricalcium phosphate and at least one further calcium phosphate-containing compound with an aqueous solution of a cohesion promoter in a concentration of 0.1 to 5% (wt/wt) based on the liquid phase, and a setting accelerator in a concentration of 0.2–5% (wt/wt), based on the liquid phase.

12. The process according to claim 11, wherein the ratio of aqueous solution to cement powder is 0.30:1–0.45:1 ml/g, the cohesion promoter is hydroxyethyl starch, soluble starch, cyclodextrin, alginate, dextransulphate, polyvinylpyrrolidone or hyaluronic acid, and the setting accelerator is $Na_2HPO_4$, $NaH_2PO_4$, $K_2HPO_4$, $KH_2PO4$ or a mixture thereof.

13. The process according to claim 11, wherein the ratio of aqueous solution to cement powder is 0.30:1–0.45:1 ml/g.

14. In a processible, settable biocement paste, suitable for the preparation of biocompatible bone cement, the improvement wherein said biocement is formed by mixing together cement powder comprising tricalcium phosphate and at least one further calcium phosphate-containing compound, and an aqueous solution containing a cohesion promoter and a setting accelerator, wherein said setting accelerator is $Na_2HPO_4$, $NaH_2PO_4$, $KH_2PO_4$, $K_2HPO_4$, or mixtures thereof, in a concentration of 0.5–5% (wt/wt), based on the liquid phase before the paste is formed.

15. A kit for the preparation of a biocement paste, comprising a cement powder comprising tricalcium phosphate and at least one further calcium phosphate-containing compound, and an aqueous solution containing a cohesion promoter and a setting accelerator, wherein said setting accelerator is $Na_2HPO_4$, $NaH_2PO_4$, $KH_2PO_4$, $K_2HPO_4$, or mixtures thereof, in a concentration of 0.5–5% (wt/wt), based on the liquid phase before the paste is formed.

16. In a method of repairing bone fractures, comprising applying a biocement paste, the improvement wherein said biocement paste is according to claim 1.

17. In a method of fixating metal prosthesis or bone screws, comprising applying a biocement paste, the improvement wherein said biocement paste is according to claim 1.

* * * * *